(12) United States Patent
Gubler (10) Patent No.: US 10,517,879 B2
(45) Date of Patent: Dec. 31, 2019

(54) DEVICE AND METHOD OF USING VOLATILE ORGANIC COMPOUNDS THAT AFFECT MOOD, EMOTION OR A PHYSIOLOGIC STATE

(71) Applicant: Performance Labs PTE. LTD., Singapore (SG)

(72) Inventor: Daniel Gubler, Orem, UT (US)

(73) Assignee: Performance Labs PTE. LTD., Singapore (SG)

( * ) Notice: Subject to any disclaimer, the term of this patent is extended or adjusted under 35 U.S.C. 154(b) by 0 days.

(21) Appl. No.: 15/380,074

(22) Filed: Dec. 15, 2016

(65) Prior Publication Data

US 2017/0173047 A1    Jun. 22, 2017

Related U.S. Application Data

(60) Provisional application No. 62/268,888, filed on Dec. 17, 2015.

(51) Int. Cl.
| | | |
|---|---|---|
| *A61K 31/56* | (2006.01) | |
| *A61B 5/1477* | (2006.01) | |
| *A61B 5/16* | (2006.01) | |
| *A61B 5/00* | (2006.01) | |
| *A61K 9/70* | (2006.01) | |
| *A61K 8/30* | (2006.01) | |
| *A61Q 13/00* | (2006.01) | |
| *A61K 8/02* | (2006.01) | |

(52) U.S. Cl.
CPC ............ *A61K 31/56* (2013.01); *A61B 5/1477* (2013.01); *A61B 5/165* (2013.01); *A61B 5/4011* (2013.01); *A61K 8/0216* (2013.01); *A61K 8/30* (2013.01); *A61K 9/70* (2013.01); *A61Q 13/00* (2013.01); *A61B 2503/42* (2013.01); *A61B 2562/0295* (2013.01); *A61K 2800/87* (2013.01)

(58) Field of Classification Search
CPC .............. A61K 2300/00; A61K 31/352; A61K 36/185; A61K 31/495; A61K 45/06; A61K 31/05; A61K 31/573; A61K 9/4858; A61K 31/192; A61K 31/337; A61K 38/1875; A61K 47/10; A61K 47/14; A61K 9/006; A61K 9/1617; A61K 31/232; A61K 31/353; A61K 31/454; A61K 31/568; A61K 31/663; A61K 38/1825; A61K 38/27; A61K 38/29; A61K 38/553; A61K 9/0031; A61K 9/1075; A61K 31/137; A61K 31/202; A61K 31/25; A61K 31/341; A61K 31/4164; A61K 31/4709; A61K 31/485; A61K 31/496; A61K 31/5383; A61K 31/5513; A61K 31/7048; A61K 33/04; A61K 33/30; A61K 36/07; A61K 38/31; A61K 9/0056; A61K 9/122; A61K 9/1676; A61K 9/209; A61K 9/5015; A61K 9/5026; A61K 9/5078; A61K 9/5084; A61K 31/00; A61K 31/01; A61K 31/015; A61K 31/122; A61K 31/19; A61K 31/357; A61K 31/4965; A61K 31/535; A61K 31/57; A61K 31/765; A61K 38/00; A61K 38/13; A61K 38/28; A61K 47/02; A61K 47/12; A61K 47/186; A61K 47/22; A61K 47/24; A61K 47/26; A61K 47/34; A61K 8/14; A61K 8/355; A61K 9/0014; A61K 9/0019; A61K 9/0053; A61K 9/0075; A61K 9/127; A61K 9/1682; A61K 9/4808; A61K 2236/37; A61K 31/20; A61K 31/355; A61K 31/445; A61K 31/4545; A61K 31/519; A61K 31/56; A61K 31/7028; A61K 36/00; A61K 8/97; A61K 9/0073; A61K 9/7023

See application file for complete search history.

(56) References Cited

U.S. PATENT DOCUMENTS

| 7,781,218 | B2  | 8/2010  | Furton |
| 2003/0109794 | A1  | 6/2003  | Phillips |
| 2010/0111895 | A1  | 5/2010  | Tuck et al. |
| 2012/0315477 | A1* | 12/2012 | Tashiro .................. A45D 34/04 428/367 |

(Continued)

FOREIGN PATENT DOCUMENTS

| CA | 2939937 | 9/2015 |
| CN | 104458353 | 3/2015 |

(Continued)

OTHER PUBLICATIONS

Albrecht, et al., "Smelling Chemosensory Signals of Males in Anxious Versus Nonanxious Condition Increases State Anxiety of Female Subjects." Chemical senses, Jan. 1, 2011, vol. 36, No. 1, pp. 19-27.

(Continued)

*Primary Examiner* — Audrea B Coniglio
(74) *Attorney, Agent, or Firm* — Knobbe, Martens, Olson & Bear LLP (57) ABSTRACT

The present invention includes an apparatus and method for aiding mood, emotion, or physiological state comprising: a substrate that is capable of capturing or absorbing one or more organic compounds from a subject having a first physiologic or emotional state at a first time; and an element that is capable of controlling the capture of the one or more organic compounds at a first time, or the release of the one or more organic compounds from the substrate at a second time, wherein exposure to an effective amount of the organic compounds changes the mood, emotion, or physiological state of the subject.

10 Claims, 5 Drawing Sheets

(56) References Cited

U.S. PATENT DOCUMENTS

| | | |
|---|---|---|
| 2014/0127326 A1 | 5/2014 | Sood |
| 2015/0057515 A1 | 2/2015 | Hagen |

FOREIGN PATENT DOCUMENTS

| | | | |
|---|---|---|---|
| WO | 1986/004238 | 7/1986 | |
| WO | WO86/04238 | * 7/1986 | ............ A61K 35/12 |
| WO | 2007/120477 A2 | 10/2007 | |
| WO | 2009/032325 A1 | 12/2009 | |
| WO | WO 2010/079490 | 7/2010 | |
| WO | WO 2013/134460 | 9/2013 | |
| WO | WO 2014/180974 | 11/2014 | |

OTHER PUBLICATIONS

Chen, et al., "Rapid mood change and human odors." Physiology & Behavior, Dec. 15, 1999, vol. 68, No. 1, pp. 241-250.
Geltsein, et al., "Human Tears Contain a Chemosignal." Science, Jan. 14, 2011, vol. 331, No. 6014, pp. 226-230.
Hanai, et al., "Analysis of volatile organic compounds released from human lung cancer cells and from the urine of tumor-bearing mice." Cancer Cell International, Feb. 24, 2012, vol. 12, No. 1, pp. 1-12.
Kwak, et al., "In search of the chemical basis for MHC odourtypes." Proceedings of the Royal Society of London B: Biological Sciences, Mar. 31, 2010, vol. 277, No. 1693, pp. 2417-2425.
Kwak, et al., "Volatile biomarkers from human melanoma cells." Journal of Chromatography B, Jul. 15, 2013, vol. 931, pp. 90-96.
Miller, et al., "Scent of a Woman: Men's Testosterone Responses to Olfactory Ovulation Cues." Psychological Science, Dec. 1, 2009, pp. 276-283.
Peled, et al., "Volatile fingerprints of cancer specific genetic mutations." Nanomedicine, Aug. 2013, vol. 9, No. 6, 758-766.
Preti, et al., "Male Axillary Extracts Contain Pheromones that Affect Pulsatile Secretion of Luteinizing Hormone and Mood in Women Recipients." Biology of Reproduction, Jun. 1, 2003, vol. 68, No. 6, pp. 2107-2113.
Shirasu, et al., "The scent of disease: volatile organic compounds of the human body related to disease and disorder." Journal of Biochemistry, Sep. 1, 2011, vol. 150, No. 3, pp. 257-266.
Stern, et al., "Regulation of ovulation by human pheromones." Nature, Mar. 12, 1998, vol. 392, No. 6672, pp. 177-179.
Vaglio, Stefano., "Chemical communication and mother-infant recognition." Communicative & integrative biology, May/Jun. 2009, vol. 2, No. 3, pp. 279-281.
European Patent Office, International Search Report and Written Opinion for PCT/IB2016/002004, dated Jul. 27, 2017, 13 pp.
Dummer, et al., "Analysis of biogenic volatile organic compounds in human health and disease", Trends in Analytical Chemistry, Vol. 30, No. 7, Nov. 7, 2011.
Abaffy et al. Comparative analysis of volatile metabolomics signals from melanoma and benign skin: a pilot study. Metabolomics, 2013, 9, 998.
Bernier et al. Analysis of human skin emanations by gas chromatography/mass spectrometry. 2. Identification of volatile compounds that are candidate attractants for the yellow fever mosquitos (*Aedes aegypti*). Anal Chem, 2000, 72, 747.
Buszewski et al. Human exhaled air analytics: biomarkers of diseases. Biomed Chromatogr, 2007, 21, 553.
Dormont et al. New methods for field collection of human skin volatiles and perspectives for their application in the chemical ecology of human-pathogen-vector interactions. J Exp Biol, 2013, 216, 2783.
Kataoka et al. Noninvasive analysis of volatile biomarkers in human emanations for health and early disease diagnosis. Bioanalysis, 2013, 5, 1443.
Kwak et al. Evaluation of bio-VOC sampler for analysis of volatile organic compounds in exhaled breath. Metabolites, 2014, 4, 879.
Merrick. Characterization of human expired breath by solid phase microextraction and analysis using gas chromatography-mass spectrometry and differential mobility spectrometry. 2005, Master Thesis, Massachusetts Institute of Technology.
Mochalski et al. Emission rates of selected volatile organic compounds from skin of healthy volunteers. J Chromatogr B, 2014, 959, 62.
Mullard. Metabolomics investigations into human apocrine sweat secretions. 2012, PhD Thesis, Univ. of Nottingham.
Rajan et al. Chemical fingerprinting of human body odor: an overview of previous studies. Malaysian J Forensic Sci, 2014, 4, 33.
Robroeks et al. Metabolomics of volatile organic compounds in cystic fibrosis patients and controls. Ped Res 2010, 68, 75.
Vaglio et al. Volatile signals during pregnancy: a possible chemical basis for mother-infant recognition. J Chem Ecol, 2009, 35, 131.

* cited by examiner

DEVICE AND METHOD OF USING VOLATILE ORGANIC COMPOUNDS THAT AFFECT MOOD, EMOTION OR A PHYSIOLOGIC STATE

CROSS-REFERENCE TO RELATED APPLICATIONS

This application claims priority to U.S. Provisional Application Ser. No. 62/268,888, filed Dec. 17, 2015, the contents of which are incorporated by reference herein in its entirety.

TECHNICAL FIELD OF THE INVENTION

The present invention relates in general to the field of compositions that effect mood, emotion or a physical state, and more particularly, to novel devices and methods for using volatile organic compounds to alter or affect mood, emotion or a physiologic state.

STATEMENT OF FEDERALLY FUNDED RESEARCH

None.

BACKGROUND OF THE INVENTION

Without limiting the scope of the invention, its background is described in connection with volatile organic compounds.

The related art shows that certain compounds are known to cause subtle changes in human behavior. For example, Miller and Maner, in an article entitled "Scent of a Woman: Men's Testosterone Responses to Olfactory Ovulation Cues" Psychological Science 21(2) 276-283, teach that using t-shirts under certain conditions (ovulation, nonovulation and control) that "ovulatory cues are detectable via chemosensory signaling and, moreover, that these cues are linked with functionally relevant endocrinological responses in men."

Preti, et al., in an article entitled "Male Axillary Extracts Contain Pheromones that Affect Pulsatile Secretion of Luteinizing Hormone and Mood in Women Recipients", Biology of Reproduction, Vol. 68, No. 6, 2107-2113 (Jun. 1, 2003), teach that human underarm secretions alter the length and timing of the menstrual cycle when applied to women recipients.

Geltsein, et al., in an article entitled "Human Tears Contain a Chemosignal," Science, Vol. 331, 226-230 (Jan. 14, 2011), show that tears contain a chemosignal as shown by looking a brain scans using functional magnetic resonance imaging of stimulated males and sniffing at tears or saline, which found that males sniffing the tears of females decreased sexual arousal. However, these authors expressly leave open the questions of "What is the identity of the active compound/s in tears? Do chemosignals in women s tears signal anything else but sexual disinterest, and is this signaling restricted to emotional tears alone? Moreover, could the emotional or hormonal state (menstrual phase/oral contraceptives) of the crier/experimenter influence the outcome? In turn, what if any are the signals in men's tears . . . or children's tears, and what are the effects of all these within, rather than across, gender?" Id. at 230.

Kwak, et al., in an article entitled "In search of the chemical basis for MHC odourtypes", Proc. R. Soc. B 2010 277, 2417-2425 (Mar. 31, 2010), teach that "Mice can discriminate between chemosignals of individuals based solely on genetic differences confined to the major histocompatibility complex (MHC)." Abstract. However, these authors conclude that "Regardless of what approach is used to focus on MHC-related odourants, their structural identification would still require isolation from the urine matrix, which, as described above, is subject to various errors." Id. at 2425.

Albrecht, et al., in an article entitled "Smelling Chemosensory Signals of Males in Anxious Versus Nonanxious Condition Increases State Anxiety of Female Subjects", Chem. Senses 36: 19-27, 2011, find that "humans in an anxious state compared with a nonanxious state are able to increase anxiety levels in other humans via their body odors" when studying sweat donation. Abstract. However, these authors state that it is not clear which secretions may have been responsible for the effects found, and that further research is required to obtain a deeper insight into brain function. Id. at 25-26.

Yet another study looking at underarm odors, by Chen and Haviland-Jones, entitled "Rapid Mood Change and Human Odors", Physiology & Behavior 68 (1999) 241-250, collected underarm odors from women and men at different stages (prepubertal, college, and older) to determine changes in depressive mood. It was found that odors could modulate the moods of other humans, with a greater reduction in depressive mood observed when smelling the odor from older women and adults. Id. at 248.

Vaglio in an article entitled, "Chemical communication and mother-infant recognition", Communicative & Integrative Biology 2:3, 279-281; May/June 2009, reviewing the literature relating to pheromones states that "Fifty years after the term pheromone was coined by Peter Karlson and Martin Lusher the search for these semiochemicals is still an elusive goal of chemical ecology and communication studies." Id. at 279.

Stern and McClintock, in an article entitled, "Regulation of ovulation by human pheromones", Nature, Vol. 392, 177-179, 12 Mar. 1998, state that their findings suggest that "These data demonstrate that humans have the potential to communicate pheromonally". Id. at 178.

Shirasu and Touhara, in an article entitled "The scent of disease: volatile organic compounds of the human body related to disease and disorder" J. Biochem. 2011; 150(3): 257-266, Jul. 19, 2011, review the literature as relates to disease conditions and volatiles obtained from breath, sweat, skin and body odor, and both disease conditions and infectious disease. Likewise, Peled, et al., in an article entitled "Volatile fingerprints of cancer specific genetic mutations", Nanomedicine: Nanotechnology, Biology, and Medicine 9 (2013) 758-766, look at patterns in volatile organic compounds emitted from cell membranes of lung cancer cells. Kwak, et al., in an article entitled "Volatile biomarkers from human melanoma cells", Journal of Chromatography B, 931 (2013) 90-96, look at volatile biomarkers from human melanoma cells. Hanai, et al., "Analysis of volatile organic compounds released from human lung cancer cells and from the urine of tumor-bearing mice", Cancer Cell International 2012, 12:7, look at volatile organic compounds in mouse urine. Finally, Dummer, et al., "Analysis of biogenic volatile organic compounds in human health and disease", Trends in Analytical Chemistry, Vol. 30, No. 7, Nov. 7, 2011, summarize the literature with regard to biogenic volatile organic compounds and biomarkers for underlying disease conditions.

SUMMARY OF THE INVENTION

Despite all these advances, a need remains for a simple, rapid way of using various observations related to pheromones to benefit the human condition.

In one embodiment, the present invention includes an apparatus for aiding mood, emotion, or physiological state comprising: a substrate that is capable of capturing or absorbing one or more organic compounds from a subject having a first physiologic or emotional state at a first time; and an element that is capable of controlling the capture of the one or more organic compounds at a first time, or the release of the one or more organic compounds from the substrate at a second time, wherein exposure to an effective amount of the organic compounds changes the mood, emotion, or physiological state of the subject. In one aspect, the element is a solvent, or a heating or cooling element that is capable of controlling the capture of the one or more organic compounds at a first time, or the release of the one or more organic compounds from the substrate at a second time. In one aspect, the one or more organic compounds from the subject having a first physiologic or emotional state are released from the subject at or about body temperature. In another aspect, the physiologic or emotional state is selected from at least one of ovulation, lactation, working out, sports activity, sexual activity, a wedding, a christening, a party, a business trip, a vacation, rock climbing, sky diving, roller coasters, bungee or cliff jumping. In another aspect, the one or more organic compounds are volatile organic compounds. In another aspect, the wherein the one or more organic compounds are selected from at least one or more sex pheromones, alarm pheromones, modulator pheromones, trail pheromones or signature odors. In another aspect, the subject is a human. In another aspect, the substrate can be reused. In another aspect, the substrate is positioned on or about the skin at the first time for sufficient time to capture the one or more organic compounds in an amount sufficient to be noticeable in the immediate surrounding of the subject upon release from the substrate. In another aspect, the substrate is selected from a carbon strip, a natural fiber, a synthetic fiber, a cellulose, a polymer, a carbon impregnated fiber, a mesh, a filter, a solid-phase microextraction fiber, a dried leaf or lichen, or a cotton gauze. In another aspect, the apparatus further comprises a housing comprising a storage area for the substrate, a power source, a heating or cooling element controller, a sprayer, an atomizer, a perfume or cologne, one or more fragrances, oils, or solvents, a propellant, a vaporizer, or a fan. In another aspect, the one or more organic compounds are released by or with a fragrance, oil, cream, lotion, shampoo, or solvent from the substrate. In another aspect, two or more substrates comprising organic compounds obtained from different moods, emotions, or physiologic states are combined prior to release. In another aspect, the two or more substrates comprising organic compounds obtained from the same mood, emotion, or physiologic state are combined prior to release.

Another embodiment of the present invention includes a method for aiding mood, emotion, or physiological state comprising: capturing one or more organic compounds from a subject having a first physiologic or emotional state at a first time on a substrate that is capable of capturing or absorbing the one or more organic compounds; and releasing the one or more organic compounds from the substrate at a second time at or about a subject in need of aiding the mood, emotion, or physiological state by smelling the one or more organic compounds associated with the mood, emotion, or physiological state. In one aspect, the step of capturing is defined further as capturing the one or more organic compounds released by the subject at or about body temperature. In another aspect, the step of capturing is conducted during a specific physiologic or emotional state in the subject, wherein the physiologic or emotional state is selected from at least one of ovulation, lactation, working out, sports activity, sexual activity, a wedding, a christening, a party, a business trip, a vacation, rock climbing, sky diving, roller coasters, bungee or cliff jumping. In another aspect, the one or more organic compounds are volatile organic compounds. In another aspect, the one or more organic compounds are selected from at least one or more sex pheromones, alarm pheromones, modulator pheromones, trail pheromones or signature odors. In another aspect, the subject is a human. In another aspect, the substrate can be reused. In another aspect, the substrate is positioned on or about the skin at the first time for sufficient time to capture the one or more organic compounds in an amount sufficient to be noticeable in the immediate surrounding of the subject upon release from the substrate. In another aspect, the substrate is selected from a carbon strip, a natural fiber, a synthetic fiber, a cellulose, a polymer, a carbon impregnated fiber, a mesh, a filter, a solid-phase microextraction fiber, a dried leaf or lichen, or a cotton gauze. In another aspect, an apparatus for use in the method is defined further as comprising a housing comprising a storage area for the substrate, a power source, a heating or cooling element controller, a sprayer, an atomizer, a perfume or cologne, one or more fragrances, oils, or solvents, a propellant, a vaporizer, or a fan. In another aspect, the one or more organic compounds are released by or with a fragrance, oil, cream, lotion, shampoo, or solvent. In another aspect, the one or more organic compounds from two or more subjects are captured concurrently.

Yet another embodiment of the present invention includes a method of determining the performance of one or more organic compounds that aid in a mood, an emotion, or a physiological state, the method comprising: a) measuring the levels of partial or total organic compounds from a subject under normal physiological conditions at a first time; b) capturing partial or total organic compounds on a substrate from the subject under different physiological conditions at a second time; c) exposing a first subset of subjects to the partial or total organic compounds from a subject under normal physiological conditions at a first time, and a second subset of the subjects to the partial or total organic compounds on a substrate from the subject under different physiological conditions at a second time; and d) determining if the to the partial or total organic compounds on a substrate from the subject under different physiological conditions at a second time shows a change in mood, emotion or physiological state that is statistically significant as compared to that of the subject exposed to the partial or total organic compounds from a subject under normal physiological conditions at a first time. In one aspect, the step of capturing the partial or total organic compounds on a substrate from the subject under different physiological conditions at a second time is conducted during a specific physiologic or emotional state, wherein the physiologic or emotional state is selected from at least one of ovulation, lactation, working out, sports activity, sexual activity, a wedding, a christening, a party, a business trip, a vacation, rock climbing, sky diving, roller coasters, bungee or cliff jumping. In another aspect, the one or more organic compounds are volatile organic compounds. In another aspect, the one or more organic compounds are selected from at least one or more sex pheromones, alarm pheromones, modulator pheromones, trail pheromones or signature odors. In another aspect, the subject is a human. In another aspect, the substrate is positioned on or about the skin at the first time for sufficient time to capture the one or more organic compounds in an amount sufficient to be noticeable in the immediate surrounding of the subject upon release from the substrate. In another aspect, the substrate is selected from a carbon strip, a natural fiber, a synthetic fiber, a cellulose, a polymer, a carbon impregnated fiber, a mesh, a filter, a solid-phase microextraction fiber, a dried leaf or lichen, or a cotton gauze. In another aspect, an apparatus for use in the method is defined further as comprising a housing comprising a storage area for the substrate, a power source, a heating or cooling element controller, a sprayer, an atomizer, a perfume or cologne, one or more fragrances, oils, or solvents, a propellant, a vaporizer, or a fan. In another aspect, the one or more organic compounds are released by or with a fragrance, oil, cream, or solvent. In another aspect, the one or more organic compounds from two or more subjects are captured concurrently.

Yet another embodiment of the present invention includes a substrate that is adapted to capture or absorb one or more organic compounds from a subject at or about body temperature, the subject having a first physiologic or emotional state at a first time, wherein the substrate is selected from a carbon strip, a natural fiber, a synthetic fiber, a cellulose, a polymer, a carbon impregnated fiber, a mesh, a filter, a solid-phase microextraction fiber, a dried leaf or lichen, or a cotton gauze, and the one or more organic compounds are selected from at least one or more sex pheromones, alarm pheromones, modulator pheromones, trail pheromones or signature odors. In one aspect, the substrate is reusable. In another aspect, the one or more organic compounds are released from the substrate by a fragrance, oil, cream, or solvent.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention includes devices and methods for capturing, storing, and using volatile organic compounds (VOCs) emitted by humans under different physiological or emotional states. The VOCs can be captured using different absorption media and used in order to elicit or trigger an emotional, mood, or physiological response from those around them. An additional application in regards to the burgeoning area of medical diagnostics is discussed. The devices and methods disclosed herein have many different applications with the potential to significantly improve mankind's quality of life.

While research over the past fifty years has demonstrated that living organisms emit a cocktail (over 200 in humans) of volatile organic compounds (VOCs) emanating off of the surface, the use of this information has been very limited. These compounds have a high vapor pressure, exhibit molecular weights under 200 amu, evaporate off of the surface of the organism at body temperature (37° C.), and readily disperse through the air. Certain single VOCs and collections of VOCs have been given the term of pheromone.

As used herein, the term "pheromone" refers to a VOC or cocktail of VOCs that are secreted or excreted from one organism, transmitted through the air via diffusion, binds to a receptor target in another member of the same species, and causes a biochemical/physiological response usually through a signal transduction cascade.

As used herein, the term "substrate" refers to a solid, gel or liquid, that will capture one or more volatile organic compounds released by a human during a defined period of time, and that can be released from that substrate at a later time with a solvent, heating or cooling. Non-limiting examples of substrates include a carbon strip, a natural fiber, a synthetic fiber, a cellulose, a polymer, a carbon impregnated fiber, a mesh, a filter, a solid-phase microextraction fiber, a dried leaf or lichen, a cotton gauze, a lotion, an oil, a gel.

As used herein, the term "element" refers to a solvent, heating, cooling, liquid, lotion, gel, or other physical change to the substrate (e.g., exposing the substrate to a mechanical, electromechanical, magnetic, radio frequency, ultrasound, infrared, radiation, ionization, and/or electrical energy) triggers the release of the captured volatile organic compounds, into a medium for later delivery using, e.g., an atomizer, a sprayer, a vaporizer, a fan, and the like.

There are several other classes of pheromones—a few of which are defined and specific examples given: Sex Pheromones—a VOC or cocktail of VOCs secreted from an organism (usually a female) during ovulation that signals time of peak fertility and attracts males of the same species. The first sex pheromone isolated and characterized was Bombykol (in 1959), which is released by the female silkworm moth to attract males. It is estimated that male moths can detect this compound over five miles away and can trace back to its origin.

Alarm Pheromones—A chemical given off by an organism during times of fear/distress that cause either a fight or flight response in members of the same species. Most species of wasps secrete a cocktail of VOCs through their skin that is picked up by members of the nest, who follow the VOC signal to the origin.

Modulator Pheromones—VOCs that can alter the timing of physiological processes in another member of the same species. Several species of livestock secrete compounds that induce synchronization of estrous cycles among female herd members.

Trail Pheromones—A volatile compound secreted and laid down on the ground by one organism that other members of the same species can follow. A majority of ant species lay down a volatile compound on their way back to the nest to indicate they have found food. Ants in the nest follow this trail until reaching the food. Some species of ant actually deposit another compound on their way back to the nest after all of the food is gone-signaling not to follow the trail anymore.

Signature Odors—A cocktail of VOCs unique to a certain member of one species that, upon repeated exposure, can immediately be recognized by another member of the same species. Several examples of this phenomenon are discussed below.

While bonafide human pheromones have not been identified in the scientific literature, there is an abundance of publications providing good evidence that the chemical odor signature in one individual can cause a physiological response in others. For example, researchers recently showed that testosterone levels of male subjects spiked when smelling the shirt worn by a women during ovulation versus smelling a shirt far from ovulation. It has also been shown that smelling the shirt of a woman far from ovulation decreases testosterone levels in men.

A paper published in Science demonstrating that female tears of sadness contain a chemosignal that, as shown by fMRI studies decrease sex drive and libido in men. Several papers regarding the major histocompatibility (MHC) complex class of proteins showing that a shirt worn by a man has a pleasant odor to women with a different MHC profile but is repulsive to women with a MHC profile similar to a man. Several studies have been published on the scent of fear showing that subjects can discriminate between cotton pads worn by people where fear has been induced versus either control cotton pads or cotton pads worn by individuals from a happy-induced state. Longtime partners can detect and sense the chemical signature of their soul mate—thus releasing a calming effect. This study was done with men sitting in a chair, blindfolded, and hooked up to physiological equipment. Different people were then brought quietly into the room and placed in close proximity to the blindfolded subject. Pronounced physiological measures of calmness and relaxation were seen when the subject's soul mate was brought in.

Depressive mood states of subjects improved from smelling a cotton pad containing VOCs from subjects in a state of happiness. McClintock et al. showed that the smelling of VOCs obtained from the underarms of women induced a synchronization of the menstrual cycles of the participants smelling the cotton pads with the menstrual cycle of the subjects wearing the pads. This phenomenon is well known among women living together. Toddlers can recognize the chemical signature of their mothers and can readily discriminate between their mothers nursing pads versus another lactating female.

An analytical instrument for detection of organic compounds is a Gas Chromatograph-Mass Spectrometer.

The present inventors have developed methods for the use of substrates that capture VOCs, which were then used to release VOCs associated with various conditions of emotion, mood, or physiological conditions. The present inventors human VOCs and demonstrate herein that different VOC profiles are emitted off of human skin under different physiological and emotional states.

Figure 1:
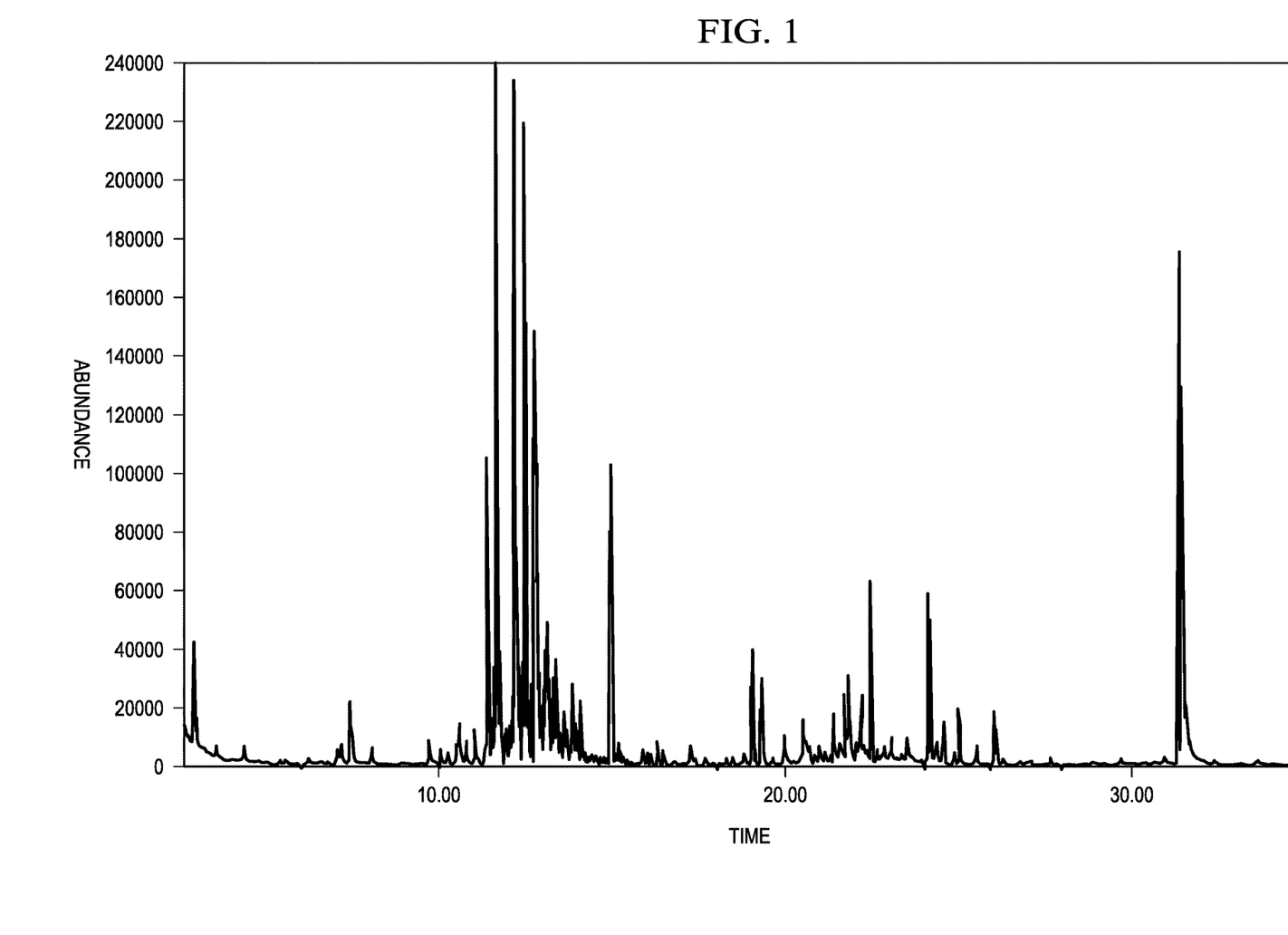
FIG. 1 shows a Gas Chromatography-Mass Spectrometer (GC-MS) spectra of volatile organic compounds (VOCs) emanating off a shirt worn by a female during ovulation and illustrates the wealth of VOCs emanating off a shirt from a female during ovulation.

FIG. 1 shows a GC-MS spectra of VOCs emanating off a shirt worn by a female during ovulation and illustrates the wealth of VOCs emanating off a shirt from a female during ovulation. Each individual peak in this spectrum represents a different VOC. VOCs were collected by incubating an activated carbon strip in a clean and capped sterilized jar containing the shirt for 8 hours. The activated carbon strip was carefully rinsed with an organic solvent and immediately injected into a GC-MS. All of the peaks between 20 and 30 minutes are absent in the spectrum of the same shirt worn by a woman far from ovulation.

Figure 2:
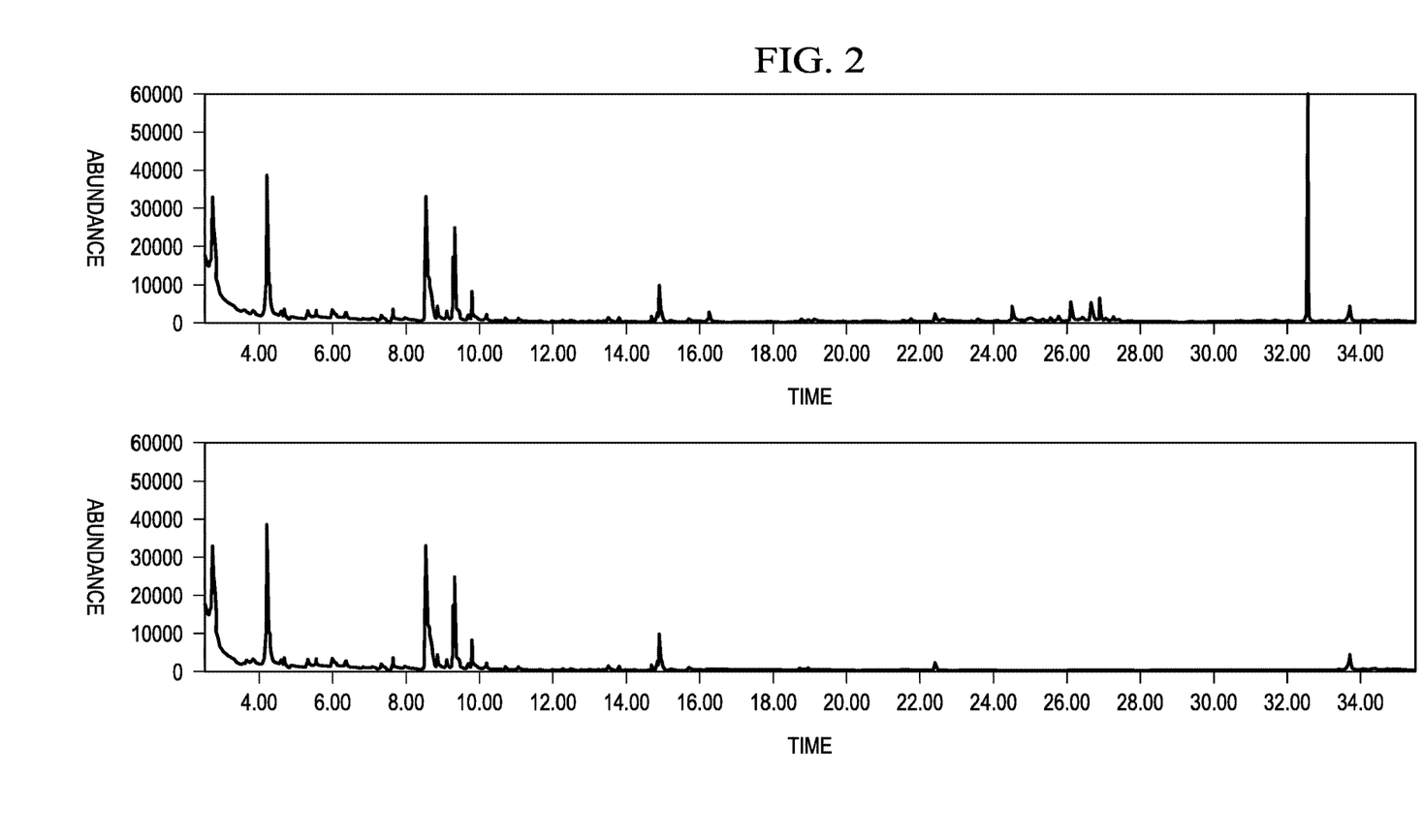
FIG. 2 shows a GC-MS spectra of the VOCs emanating off of a shirt worn by a subject in a neutral state before induction of fear (bottom spectrum) and after fear is induced (top spectrum) in the participant. Notice the presence of VOCs in the 24-28 minute range on the spectrum in the fear state (top spectrum) versus a neutral state (bottom spectrum).

FIG. 2 shows a GC-MS spectra of the VOCs emanating off of a shirt worn by a subject in a neutral state before induction of fear (bottom spectrum) and after fear is induced (top spectrum) in the participant. Notice the presence of VOCs in the 24-28 minute range on the spectrum in the fear state (top spectrum) versus a neutral state (bottom spectrum).

Figure 3:
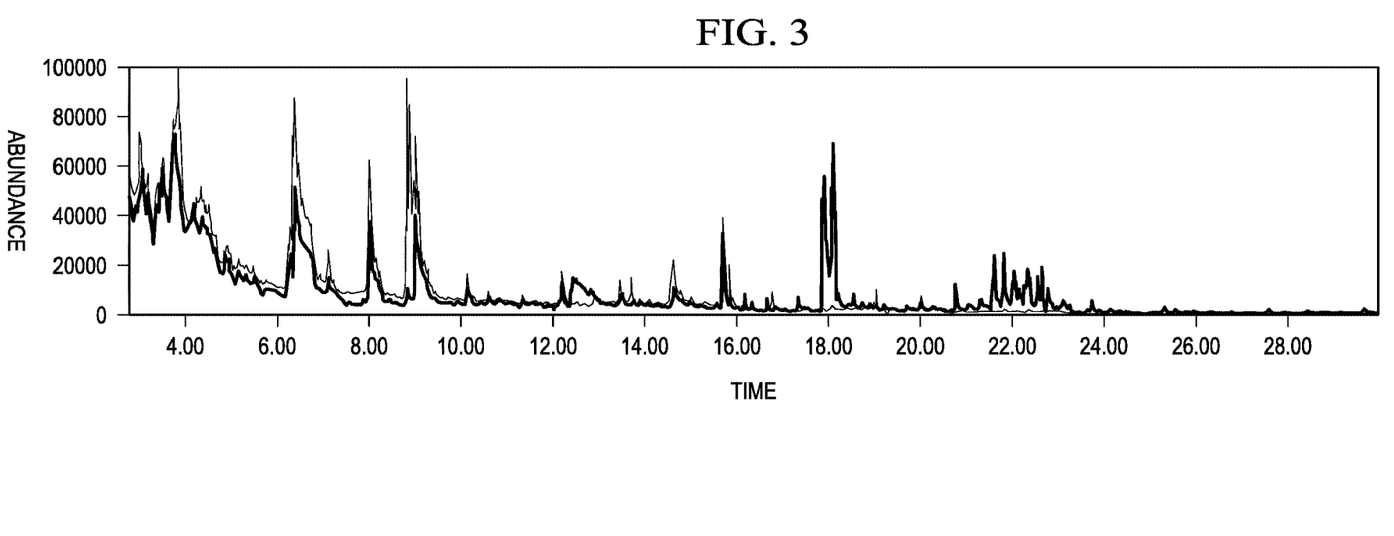
FIG. 3 shows two different GC-MS traces overlaid on top of each other demonstrating the difference in chemical composition of human tears with no stimulus (red) and when sad (black). The biggest change is seen between 18 and 24 minutes in the spectra.

FIG. 3 shows two different GC-MS traces overlaid on top of each other demonstrating the difference in chemical composition of human tears with no stimulus (red) and when sad (black). The biggest change is seen between 18 and 24 minutes in the spectra.

Shown in the figures below are the different materials and instrumentation used to validate and apply the concepts of this invention. An activated carbon strip, commonly used in forensic arson analysis, has the ability to absorb VOCs emanating from human skin. The ability of activated carbon to absorb VOCs arises from the extremely large surface area of the material. The present inventors have found that a normal amount of time for equilibrium to be established in absorbing human VOCs is about 4 hours.

Activated carbon strips are commercially available from forensics suppliers (like Albrayco Technologies, Inc.) and come in a 100-count jar that has been flushed and sealed under inert gas (argon) to ensure sterility and purity.

Figure 4:
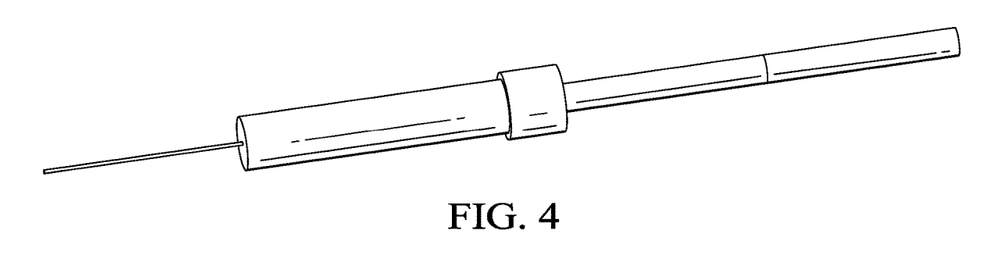
FIG. 4 shows a device for a solid phase microextraction (SPME) fiber that can also be used to absorb VOCs from the body.
Figure 5:
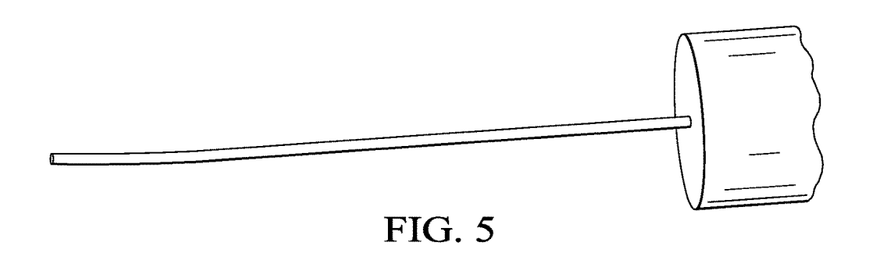
FIG. 5 shows a close-up picture of the white SPME fiber coming out of the syringe needle.

FIG. 4 shows a housing for a solid phase microextraction (SPME) fiber that can also be used to absorb VOCs from the body. SPME fibers are composed of several different organic polymers and are quite good at absorbing VOCs. The time for equilibrium to be established in absorbing human VOCs is about 1 hour. FIG. 5 shows a close-up picture of the white SPME fiber coming out of the syringe needle.

Cotton gauze pads also have the ability to absorb VOCs from humans. Lichens are also a medium that can be used for this application—as lichens readily absorb VOCs. In summary, the materials mentioned in this invention with the ability to human absorb VOCs are activated carbon strips, SPME fibers, cotton gauze pads, and lichens.

A Gas Chromatography-Mass Spectroscopy (GC-MS) instrument is the analytical instrument of choice used to identify and quantify the VOCs absorbed by the different types of material mentioned above. The SPME fiber is inserted directly into the injection port of the GC-MS. If using the activated carbon strip, a little bit of an organic solvent (like dichloromethane) is used to elute the VOCs off of the strip and then injected into the GC-MS. In the lichen application, ground and dried lichen is rinsed several times with a small amount of organic solvent and then injected into the GC-MS. In the application using a cotton gauze pad, the pad is eluted off with a minimum amount of an organic solvent and then analyzed by GC-MS.

While the scientific literature has recognized human VOCs, the present invention is based on the novel combination of new material science to this VOC chemistry to create a novel device using novel methods, as well as, a commercially viable application.

Briefly, one example of the present invention works as follows: a woman would take an activated carbon strip that has been stored under inert conditions and would wear it in close proximity to the skin (likely in her bra strap) for around 8 hours. One non-limiting example of a good time to do this would be in the evening before retiring to bed. The activated carbon strip can be provided in, or be inserted into, a soft, generally non-absorbent material, pouch, sleeve or other retainer or container that permits contact with, and absorption of, the VOCs emanating from the user into or onto the activated carbon strip. The carbon strip can be a made up of solely activated carbon, but can also be an activated carbon coating that is on, in, or about a material or substrate to which the activated carbon is attached, glued, coated, adhered, encapsulated, or otherwise retained. Upon waking in the morning the woman would take the activated carbon strip and put the strip directly into a small fragrance atomizer with her favorite perfume (FIGS. 6-9) or other solvent that would be selected to maximize capture of the VOCs.

The strip would be left to soak in the atomizer for 1, 2, 3, 4, 5, 6, 7, 8, 9, or 10 minutes, upon which it would be taken out of the atomizer and discarded. If the activated carbon strip is left in the perfume for a prolonged time it will start to absorb the VOCs in the perfume. Upon removing the activated carbon strip from the atomizer, it is discarded. Generally, these strips aren't reusable for this technology.

The perfume or solvent would be applied as normal—except that now her favorite perfume contains her VOC chemical signature produced during, e.g., ovulation. Thus, the user can supplement or be added to the VOCs that are normally produced, with the stored VOCs, thus enhancing or amplifying this signal. The present invention can be used to enhance her attractiveness by increasing men's testosterone levels (see FIG. 1). Based on stability studies, the VOCs in the perfume can degrade decompose over time, with an effective amount of VOCs generally storable for about 3-4 weeks—upon which another new activated carbon strip would be used and the process repeated.

Figure 6:
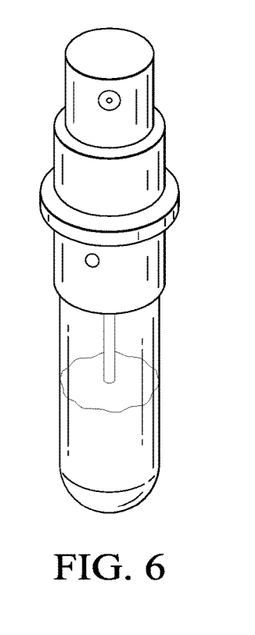
FIG. 6 shows that once the VOCs from the body are absorbed onto the activated carbon strip, it can then be put into a small atomizer (like the one below already containing an activated carbon strip) and a small amount of your favorite perfume/cologne is added.

FIG. 6 shows that once the VOCs from the body are absorbed onto the activated carbon strip, it can then be put into a small atomizer and a small amount of your favorite perfume/cologne is added. The organic solvents in the perfume/cologne remove the VOCs from the activated carbon strip into the liquid perfume/cologne, which can then be stored and later applied on the skin as you would any other fragrance. Thus, the user is able to store and amplify their own chemical signature to a perfume/cologne and later deposit it on the user's skin. This method supplements the user's skin with your natural VOC profile captured during a particular physiological state (e.g., during ovulation, lactation, working out, sports activity, sexual activity, a wedding, a christening, a party, a business trip, a vacation, rock climbing, sky diving, roller coasters, bungee or cliff jumping) that can enhance the VOC signal given off (e.g., increase the likelihood of attracting a mate in the ovulation case). Likewise, the user could seek to prevent attracting the attention of another by selecting the applicable time and place to capture VOCs.

Figure 7:
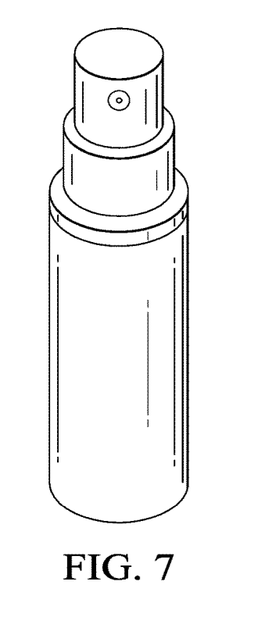
FIG. 7 shows an atomizer with the outside sleeve in which the activated carbon strips and the atomizer are provided together.
Figure 8:
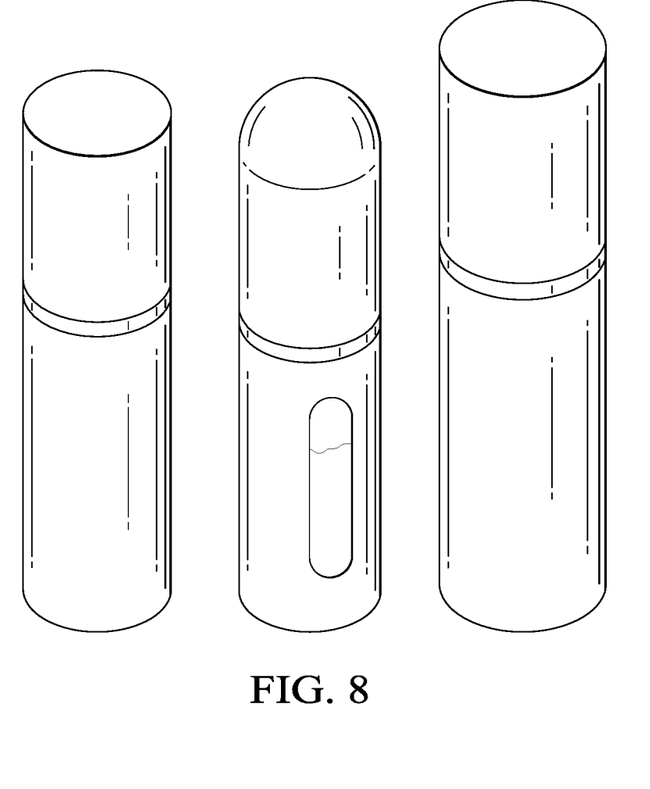
FIG. 8 shows different atomizers that could be used in this commercial application.

FIG. 7 is a picture of the atomizer with the outside sleeve put on. This atomizer can be readily designed to look nice for a commercial application in which the activated carbon strips and the atomizer would be sold together. FIG. 8 shows additional examples of a few of the many different atomizers that could be used in conjunction with the present invention and in this example a specific commercial application.

This novel approach has several benefits over the commercially available pheromone products currently on the market, because: (1) contrary to popular belief, bonafide human pheromones have not been discovered/reported in the scientific literature; (2) the pheromone products on the market today contain large amounts of compounds like dihydroepiandrostenone (DHEA) and other steroids that, while there is evidence for these compounds being sex pheromones in swine, have not been validated in human subjects; (3) pheromones are usually not a single VOC but, rather and cocktail of VOCs; and (4) this application captures the complete suite of VOCs coming off of a female under this physiological state and deposits the whole VOC profile into the perfume.

The Anti-Love Potion #9 Application. The idea for this application is the same as the Love Potion #9 application except that a female would wear the activated carbon strip when she is far from ovulation, deposit this strip into her perfume atomizer, and use as desired. This idea could be used, if desired, as an additional layer of contraceptive protection and would be applicable to women anywhere.

Additionally, an activated carbon strip can be worn during times of sadness/crying to provide the same general class of chemical messengers (e.g., VOCs) as when far from ovulation. The user wears their own VOC signature produced during a particular emotional or physiological state.

Male Major Histocompatibility (MHC) Protein Application. Of course, the present invention is not limited to females, but rather can be used to attract others. Based on the MHC protein research, men can use the present invention to increase their chances of finding a companion with a different MHC profile. Men would wear a carbon strip, preferably when exercising, and would deposit the strip into a fragrance atomizer containing their favorite cologne for ~5 minutes before taking out and discarding. The application is similar to the two female applications mentioned above in that this is amplifying or accentuating the VOC profile of the individual wearing it. This is the men's version of the Love Potion #9.

The Calming/Soothing Application. This application takes advantage of VOCs released while in close proximity to one's soul mate to have a calming effect (presumably through transmission of VOCs through the air). In this application a person could put an activated carbon strip worn by their soul mate into their fragrance—thus providing the calming VOCs of their soul mate to the individual when they are apart (e.g. on a business trip, or otherwise apart for an extended period of time). In one aspect, the VOCs can be captured concurrently by both users to capture the VOCs of both parties at the same time. Thus, the user can recreate the common VOCs at a later time.

General Emotional State Application (e.g. Happiness, Confidence, etc.). In this application the VOCs are captured coming off of a person under any emotional state. Some other applications (not an exhaustive list, by any means) could be the following: (1) wearing the strip when feeling extra happy and applying it to your fragrance. Could be used when you need a pick-me-up or perhaps to help with depressive mood states. (2) confidence is an interesting mood state studied in the psychological literature that could be harnessed by wearing a strip during these times and applying it to your fragrance. This could be worn when going to a job interview, giving a big presentation at work, at a general business meeting, etc. (3) VOCs could be collected when doing something adventurous (rock climbing, sky diving, roller coasters, bungee jumping, etc.), put in a fragrance, and worn when desired. (4) Anger is known to produce a distinct VOC profile. Perhaps a useful application could be found for this.

The Essential Oil Application. The present invention is not limited only to putting the activated carbon strip into a fragrance atomizer and applying it on the skin. Alternatively, the activated carbon strip could be dipped into an essential oil and then used in a diffuser. An alternative route to the atomizer/perfume route is the essential oil/diffuser application. The activated carbon strip laden with human VOCs could be put into a diffuser with an essential oil. The organic compounds in the essential oil would elute the VOCs from the carbon strip into the oil. The diffuser would then revolatilize these VOCs into the air. An application for this route would be for a spouse to place an activated carbon strip worn by their soul mate into the diffuser to release VOCs that have a calming, anti-anxiety effect. A mother could put an activated carbon strip of her scent into a diffuser located in her child's room (in conjunction with an essential oil like lavender) to calm the child while sleeping. There are many other applications that could be used with this essential oil diffuser depending on the emotional or physiological state captured by the activated carbon strip.

Customized Skin Care Products Applications. Human VOCs absorbed onto a material like an activated carbon strip could lead to other applications besides putting it in a fragrance atomizer or an essential oil diffuser. The VOCs from a person could be used to create an individualized personal care line. The person could send in their activated carbon strip worn under a certain condition (e.g. a female during ovulation), which would then be extracted with small amounts of the organic solvents used in personal care products. The VOC extract could then be incorporated into different personal care products that would be distinct for the individual.

Medical Diagnostics Application. Using the present invention the user is able to capture human VOCs that can be applied to the area of non-invasive medical diagnostics. Some have shown that certain VOCs are emitted from the body under different disease states including diabetes, high cholesterol, cancer, liver disease, Alzheimer's, schizophrenia, and several others. Hundreds of biomarker compounds for these medical conditions and others are known in the scientific literature. The state of the art in the field of medical diagnostics is being able to detect disease states early enough without needing to perform surgery in order to diagnose.

The medical application has a user wear the activated carbon strip and then run it through a GC-MS using a customized method that has been programmed to detect all of the VOCs in the literature that are indicative of a disease state. If one of these compounds is detected, an alert is set when a certain VOC is detected by the GC-MS, that was detected and the disease state associated with that VOC. The results of this method would then trigger further tests aimed at confirmation and/or an initial direction for treatment or a change in treatment. One aspect of this technology is that it is a non-invasive early detection medical diagnostic application that could help to identify disease state at very early stages and help to save lives. The VOC profile of an individual changes right as the disease state is forming that can't be seen in normal cell culture assays because the cellular morphology has not become evident yet.

Another application of this technology would be to have a portal that a person would stand in with a GC-MS instrument attached to the portal. The design of such an instrument would be similar to the trace explosive portals designed by Smiths Detection and others. A VOC detection portal (such as the portal particle analyzer) can be used as an early screening tool in doctor's offices and hospitals for early disease detection. This instrument would have tremendous advantages over animals capable of detecting VOCs in disease or the other technologies currently available.

Thus, the present invention can use several different mediums to absorb VOCs, which can then be deployed by a user at a specific time and place to harness emotional/physiological states and in medical diagnostics.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for modulating mood or emotion comprising:
   capturing one or more organic compounds from a subject experiencing a specific mood or emotional state on a substrate that is capable of capturing or absorbing the one or more organic compounds, wherein the substrate is an activated carbon strip, a carbon impregnated fiber, or a solid-phase microextraction fiber, and wherein the one or more organic compounds are captured by wearing the substrate in close proximity to the skin for a time period of at least one hour;
   releasing the one or more organic compounds from the substrate into a fragrance, oil, cream, lotion, or shampoo; and
   exposing the one or more organic compounds to the subject, thereby modulating mood or emotion.

2. The method of claim 1, wherein the step of capturing is defined further as capturing the one or more organic compounds released by the subject at or about body temperature.

3. The method of claim 1, wherein the step of capturing is conducted during a specific mood or emotional state in the subject, wherein the mood or emotional state takes place during a time selected from at least one of ovulation, lactation, working out, sports activity, sexual activity, a wedding, a christening, a party, a business trip, a vacation, rock climbing, sky diving, roller coasters, bungee or cliff jumping.

4. The method of claim 1, wherein the one or more organic compounds are volatile organic compounds.

5. The method of claim 1, wherein the one or more organic compounds are selected from at least one or more sex pheromones, alarm pheromones, modulator pheromones, trail pheromones or signature odors.

6. The method of claim 1, wherein the subject is a human.

7. The method of claim 1, wherein the substrate can be reused.

8. The method of claim 1, wherein the substrate is positioned on or about the skin at the first time for sufficient time to capture the one or more organic compounds in an amount sufficient to be noticeable in the immediate surrounding of the subject upon release from the substrate.

9. The method of claim 1, wherein an apparatus for use in the method is defined further as comprising a housing comprising a storage area for the substrate, a power source, a heating or cooling element controller, a sprayer, an atomizer, a perfume or cologne, one or more fragrances, oils, or solvents, a propellant, a vaporizer, or a fan.

10. The method of claim 1, wherein the one or more organic compounds from two or more subjects are captured concurrently.

* * * * *